US005719051A

United States Patent [19]

Mundt et al.

[11] Patent Number: 5,719,051
[45] Date of Patent: Feb. 17, 1998

[54] PERFUSION SYSTEM AND A METHOD FOR THE LARGE SCALE PRODUCTION OF VIRUS OR VIRUS ANTIGEN

[75] Inventors: Wolfgang Mundt, Vienna; Noel Barrett, Klosterneuburg/Weidling; Friedrich Dorner; Johann Eibl, both of Vienna, all of Austria

[73] Assignee: Immuno Aktiengesellschaft, Vienna, Austria

[21] Appl. No.: 357,292

[22] Filed: Dec. 13, 1994

Related U.S. Application Data

[63] Continuation of Ser. No. 861,882, filed as PCT/AT90/00128, Dec. 21, 1990 published as WO91/09935, Jul. 11, 1991, abandoned.

[30] Foreign Application Priority Data

Dec. 22, 1989 [AT] Austria ............................ 2928/89

[51] Int. Cl.$^6$ ........................ C12N 7/02; C12N 7/01
[52] U.S. Cl. .................. 435/235.1; 435/239; 435/174; 435/176; 435/177; 435/364
[58] Field of Search ..................... 435/235.1, 239, 435/174, 176, 177

[56] References Cited

U.S. PATENT DOCUMENTS

| | | | |
|---|---|---|---|
| 4,072,565 | 2/1978 | Weiss et al. | 435/235.1 |
| 4,525,349 | 6/1985 | Montagnon et al. | 435/235.1 |
| 4,699,785 | 10/1987 | Pederson | 435/235.1 |
| 5,391,491 | 2/1995 | Mundt et al. | 435/240.2 |

FOREIGN PATENT DOCUMENTS

| | | |
|---|---|---|
| 142343 | 10/1980 | Denmark. |
| 066 726 | 12/1982 | European Pat. Off.. |
| 239 648 | 9/1986 | European Pat. Off.. |
| 2 444 466 | 12/1979 | France. |
| 201799B | 12/1990 | Hungary. |
| 60-102187 | 6/1985 | Japan. |
| 2-78634 | 3/1990 | Japan. |
| 447789 | 12/1986 | Sweden. |
| 2 059 991 | 9/1980 | United Kingdom. |
| 2 094 832 | 3/1982 | United Kingdom. |
| 2 151 610 | 12/1982 | United Kingdom. |

OTHER PUBLICATIONS

J. Buzek, Separation of Time–defined Avian Myeloblastosis Virus(AMV) Using Column Cultivation of Leukaemic Myeloblasts, Institute of Organic Chemistry and Biochemistry, pp. 97–100 (Aug. 20, 1975).

Greenwalt, et al., A New Method for Preparing Buffy Coat–Poor Blood, Tranfusion, vol. 2 pp. 221–229 (1962).

Yale Rabinowitz, Separation of Lymphocytes, Polymorphonuclear Leukocytes and Monocytes on Glass Columns, Including Tissue Culture Observations, Blood, vol. 23, No. 6, pp. 811–828 (Jun. 1964).

Hoke, et al, "Protection Against Japanese Encephalitis By Inactivated Vaccines," *New England Journal of Medicine*, 319:608–614, (1988).

Kunz, et al. "Immunogenicity and Reactogenicity of a Highly Purified Vaccine Against Tick–bone Encephalitis", *Journal of Medical Virology*, 6:103–109, (1980).

Jackwood et al. "Replication of Infectious Bursal Disease Virus in Continuous Cell Lines," *Avian Diseases*, 21(2): 370–375 (1986).

Florentine et al. *Dev. Biol. Stand.* 60: 421–430 (1985).
Widell et al. *J. Virol. Methods* 8: 63–71 (1984).
Griffiths et al. *Develop. Biol. Standard* 50: 103–110 (1982).
Reuveny et al. *Dev. Biol. Stand.*, 60: 243–253 (1985).
Lazar et al. *Dev. Biol. Stand.*, 60: 457–465 (1985).
caij et al. *Arch Virol*, 105: 113–118 (1989).
Buzek, *Folio Biol.* 22(2) 1976, pp. 97–100 (Biosis ABS).
Poindinger et al. *J. of Gen Virology.* 1991 pp. 573–578.
Smith et al. *J. of Clinical Mocrobiology* 1984, pp. 267–272.
Deryabin et al. *VOPR Virusol* (2), 1975 pp. 235–238. (See Biosis Abstract).

*Primary Examiner*—Blaine Lankford
*Attorney, Agent, or Firm*—Foley & Lardner

[57] ABSTRACT

The invention resides in a matrix, i.e. in a carrier material, with human or animal cells adherently bound thereto, the cells being infected with virus. It has shown that surface-dependent cells suitable for virus propagation remain adherently bound to a matrix even in the virus-infected state, continuously produce virus antigen over relatively long periods of time and deliver them into the culture medium. For producing TBE virus antigen by growing tick-borne encephalitis (TBE) virus in cell cultures, a surface-dependent permanent cell line, preferably the Vero cell line ATCC CCL 81, is inoculated with TBE virus, and the cells are kept bound to carriers in a non-lyric serum-free system while maintaining the cell growth, so as to maintain antigen formation, whereupon the antigen-containing medium is separated form the carrier-bound cells and, in a known manner, is processed to a galencially acceptable preparation by concentration, inactivation and purification.

9 Claims, No Drawings

PERFUSION SYSTEM AND A METHOD FOR THE LARGE SCALE PRODUCTION OF VIRUS OR VIRUS ANTIGEN

This application is a continuation of application Ser. No. 07/861,882, filed Jun. 22, 1992, now abandoned (which is a National Phase of PCT/AT90/00128 filed on Dec. 21, 1990, published as WO91/09935, Jul. 11, 1991) now abandoned.

The invention relates to a matrix with human or animal cells adherently bound thereto, as well as to a method of producing virus/virus antigen, in particular tick-borne encephalitis (TBE) virus antigen.

Infections with the virus of TBE have been observed in Europe since World War II. In Austria, in Southern Germany and in Czechoslovakia, several hundred patients are stationarily treated each year because of a TBE infection.

The TBE virus is assigned to the group of flaviviruses of the earlier serological group B of the arboviruses, which constitutes a genus of the Togaviridae virus group.

Inactivated vaccines against one of the most important and most frequent encephalitis pathogens in man, the Japanese encephalitis B virus, have been available for some time. These inactivated vaccines are recovered from the brains of infected mice, purified, and are acknowledged to be safe and effective (Hoke et al., N. Engl. J. Med., 319, 608 (1988)).

Since 1976 a vaccine against TBE has been available and admitted by the health authorities. For producing this vaccine, the virus is grown in the brains of infected baby mice, propagated in chick embryo cells, inactivated with formalin and subsequently subjected to an efficient purification procedure (Heinz et al., J. Med. Virol., 6, 103 (1980)).

In the literature a number of possibilities for propagating arboviruses with a view to the possible production of a vaccine have been described. The method mostly used today is the inocculation of chick embryo fibroblasts with a TBE seed virus recovered from a mouse brain, and the cultivation of the inocculated cells. This method requires a complicated purification of the antigen so as to remove complex, heterological biological material and so as to avoid a sensitizing effect in the persons to be vaccinated when repeatedly administering vaccine doses obtained therefrom.

For providing chick embryo cells, one has to depart from SPF (=specific pathogen free) eggs. These SPF eggs must be subjected to a great number of time-consuming examinations to maintain their SPF status prior to each use.

Furthermore, chick embryo cell cultures exhibit only low generation numbers in continued culturing, thereby limiting the size of batches, the primary culture was difficult to keep sterile and the quality of the primary cells with regard to virus propagation and antigen production was not constant.

These disadvantages exist not only with the methods of producing TBE virus antigen, but exist quite generally in the production of antigens.

The invention has as its object to improve the production of virus/virus antigen, in particular of TBE virus/virus antigen such that the above-mentioned disadvantages are eliminated, and to provide a method of growing virus/virus antigen in cell cultures which particularly enables production on a large scale, wherein simultaneously the culture can be maintained sterile in a simple manner. Furthermore, the delivery of undesired cellular proteins into the culture supernatant is to be minimized.

For obtaining the above indicated objects, a matrix is provided, i.e. a carrier material, having human or animal cells adherently bound thereto, the cells being infected with virus. The invention is based on the finding that surface-dependent cells suitable for virus propagation remain adherently bound to a matrix even in the virus-infected state, continuously produce virus antigen over relatively long periods of time and deliver it into the culture medium.

It is possible to store the matrix according to the invention loaded with infected cells for several days at a temperature of between 0° C. and 8° C., i.e. under conditions under which the cell metabolism and thus the virus production are stopped. A matrix thus stored may later on be used for producing virus antigen without any problems, by introducing it into a culture medium and adjusting the respective growth conditions. The matrix according to the invention thus constitutes a starting culture capable of being produced in stock at constant quality and activity, whose sterile condition is easy to check and which may be used for virus antigen production at any time.

The binding of the antigen-producing cells to the carrier furthermore allows for an extremely simple handling of the virus infected cells that are ready for production. Thus it is, e.g., possible to carry out the virus/virus antigen production continuously in a perfusion reactor. Separation of the cells from the antigen-containing medium is substantially facilitated by their being bound to the matrix, whereby the matrix according to the invention simplifies the commercial-scale production of virus/virus antigen.

A preferred embodiment of the matrix according to the invention consists in that Vero cells ATCC CCL 81 are provided as the adherently bound cells, which preferably are provided for the production of TBE virus antigen and thus are infected with TBE virus.

The cells adherently bound to the matrix may, however, also be infected with flavivirus or with arena virus.

Glass, cross-linked dextran, gelatine or synthetic material has proved to be well suited as the material for the matrix, it being best if the matrix is formed as a microcarrier whose particle diameter preferably is in the range between 100 µm and 3000 µm. These microcarriers may have a smooth surface or a porous structure.

A further suitable embodiment of the matrix according to the invention is characterised in that between $1 \times 10^5$ and $4 \times 10^5$ cells are adherently bound to its surface per $cm^2$ thereof.

The invention also relates to a method of producing TBE virus antigen by using the matrix according to the invention, which is charaterised in that the surface-dependent permanent cells, preferably the Vero cells ATCC CCL 81, are inoculated with the TBE virus, and the cells are kept adherently bound to a matrix in a serum-free medium while maintaining their viability so as to maintain an antigen formation and an antigen delivery into the medium, whereupon the antigen-containing medium is separated from the carrier-bound cells and is processed to a galenically acceptable preparation in a known manner by concentration, inactivation and purification.

The Vero cell line ATCC CCL 81 is obtained from the kidney tissue of the green monkey (*Cercopithecus aethiops*) and may be kept metabolically active in serum-free medium. For such a permanent cell line, a mother seed cell bank and a working seed cell bank are started and all the tests for contaminating substances are carried out. This permanent cell line thus can be precisely characterised not only with regard to its freedom from contaminating microorganisms, but also with regard to is growth behaviour, starting culture, propagation behaviour, and, once optimized, may be considered as constant.

With the method according to the invention, preferably Vero cells bound to microcarriers are used. Thereby a high cell density can be obtained which, with the primary cell cultures hitherto used, could be obtained neither in Roux flasks nor in suspension, and which enables a considerable increase in virus and virus antigen yields per fermentation volume.

An advantageous embodiment of the method according to the invention consists in that virus propagation and antigen formation are carried out in a continuously operated perfusion reactor for a period of at least 5 days, at a temperature of between 34° and 37° C., wherein perfusion may be effected at a perfusion rate of from 0.3 to 10 v/v/day. Furthermore, in the perfusion reactor there may be provided a cell density of from $2 \times 10^9$ to $2 \times 10^{10}$ cells per liter of fermentation volume, the latter in a fluidized bed fermenter.

The virus propagation of the invention in a perfusion culture enables a substantial reduction of the—perfusion-rate dependent—dwell time of the virus and of the virus antigen in the medium as compared to that of the cultivation in batches. The shorter dwell time causes a much slighter thermal inactivation and thus results in a higher productivity of the method according to the invention. Thus, an antigen concentration of from 1 to 10 µg/ml may be reached and maintained in the perfusion medium.

With the method according to the invention, optimum conditions for cultivation may be adjusted in a simple manner. Furthermore, substantially less manipulations are required for its execution than with all the known methods, thus making handling of the infectious material safer and enabling continuous and quick working up of the virus and of the virus antigens from the culture medium.

In the following, the production of the virus inoculum, the culture of the cells for the virus and virus antigen production, and the virus and virus antigen production as such will be described in more detail.

1. Virus inoculum

Cells (e.g. Veto ATCC CCL 81) are cultivated in Roller flasks at 37° C. up to confluence and infected with 1 ml of a seed virus suspension. Starting from the 2nd day after infection, half the medium is replaced with serum-free medium each day. The medium supernatants from the 4th to the 8th day contain $2-5 \times 10^7$ p.f.u. per ml and are stored at −20° C. until they are used as virus inoculum.

2. Culturing the cells for the virus/virus antigen production

Starting from the ATCC CCL 81 working seed cells stored in liquid nitrogen, these cells are propagated in tissue culture flasks until an amount of cells is obtained which allows inoculation of a fermenter. Further culturing of the cells is effected in fermentation vessels at 37° C., and as much surface as possible should be provided for adherence of the adheringly growing working seed cells. Such large surfaces are obtained by using Roller flasks of glass or of polystyrene of by using microcarriers (MC). MC of cross-linked dextran having a size of between 170 µm and 250 µm are best suited.

The MC loaded with seed cells are cultured at 37° C. until a cell density of from $1 \times 10^5 - 4 \times 10^5$ cells per cm² has been reached. Generally, this cell density is reached after six days. During culturing, the microcarrier is completely overgrown with cells, and finally individual microcarriers may grow together to groups via the cell sheet adhering to their surfaces.

3. Virus/virus antigen production

When the cell density indicated has been reached, the cells bound to MCs are infected with the virus inoculum (1–0.01 pfu/cell, preferably 0.1 pfu/cell) to produce the matrix according to the invention. The matrix according to the invention may be stored for several days at a temperature of between 0° C. and 8° C. or it may immediately be used for the production of virus antigen.

For the production of antigen, the MCs loaded with infected cells are introduced into a perfusion reactor. From this time of virus infection onwards, only serum-free medium will be used in the culture, which is pumped continuously through the perfusion reactor, while the cells cultured on the microcarriers are retained in the reactor by a retention arrangement. Starting from the 2nd day post infection, virus antigen in a high concentration is present and may be continuously recovered therefrom for at least 10 days.

The method according to the invention will be explained in more detail by way of the following Examples. Determination of the virus antigen was effected in all the Examples with an antigen-ELISA.

EXAMPLE 1

Vero cells ATCC CCL 81 were cultured in a 6-1-fermenter on microcarriers (Cytodex 3 of Pharmacia) at 37° C. up to a cell number of $2 \times 10^6$ per ml of culture medium (DMEM= Dulbecco's Eagle Medium), and a) was infected with TBE virus (0.1 pfu/cell), and virus propagation was effected in batches.

TABLE 1

| Days post infection | virus/virus antigen µg/ml |
|---|---|
| 2 | 0.20 |
| 3 | 0.70 |
| 4 | 1.60 |
| 5 | 2.70 |
| 6 | 4.00 |
| 7 | 3.80 |
| 8 | 2.90 |

The productivity amounted to 4 mg of virus/virus antigen per 1 of fermentation volume.

b) was infected with TBE virus (0.1 pfu/cell) and culture medium was continuously perfused at 0.5 volumes/fermenter volume/day.

TABLE 2

| Days post infection | virus/virus antigen µg/ml |
|---|---|
| 2 | 0.30 |
| 3 | 1.60 |
| 4 | 4.50 |
| 5 | 4.50 |
| 6 | 2.50 |
| 7 | 3.20 |
| 8 | 2.90 |
| 9 | 2.50 |
| 10 | 2.30 |

The productivity amounted to 13.7 mg of virus/virus antigen per 1 of fermentation volume.

c) was infected with TBE virus (0.1 pfu/cell) and culture medium (DMEM) was continuously perfused at 1 volume/fermenter volume/day.

TABLE 3

| Days post infection | virus/virus antigen µg/ml |
|---|---|
| 2 | 0.45 |
| 3 | 1.40 |
| 4 | 2.00 |
| 5 | 2.00 |
| 6 | 1.70 |
| 7 | 1.60 |
| 8 | 1.10 |
| 9 | 1.10 |
| 10 | 0.90 |

The productivity amounted to 12.4 mg of virus/virus antigen per 1 of fermentation volume.

EXAMPLE 2

Vero cells (ATCC CCL 81) were cultured in as 40-1-fermenter on microcarriers (Cytodex 3 of Pharmacia) at 37° C. up to a cell number of $2\times10^6$ cells/ml and, after infection with TBE virus (0.1 pfu/cell), continuously perfused with medium (DMEM) (0.33 vol/fermenter volume/day).

TABLE 4

| Days post infection | virus/virus antigen µg/ml |
|---|---|
| 2 | 1.60 |
| 3 | 3.50 |
| 4 | 5.00 |
| 5 | 4.30 |
| 6 | 4.00 |
| 7 | 2.90 |
| 8 | 2.70 |
| 9 | 2.10 |
| 10 | 2.00 |

The productivity amounted to 10.7 mg of virus/virus antigen per 1 of fermentation volume.

EXAMPLE 3

Vero cells (ATCC CCL 81) were cultured in a 40-1-fermenter on microcarriers (Cytodex 3 of Pharmacia) at ° C up to a cell number of $3\times10^6$ cells/ml and continuously perfused with medium (DMEM) (1 vol/fermenter volume/day) after infection with TBE virus (0.1 pfu/cell).

TABLE 5

| Days post infection | Virus/virus antigen µg/ml |
|---|---|
| 2 | 1.10 |
| 3 | 3.80 |
| 4 | 3.90 |
| 5 | 3.00 |
| 6 | 2.30 |
| 7 | 2.20 |
| 8 | 2.00 |
| 9 | 3.15**) |
| 10 | 2.30 |

**)The perfusion rate was reduced to 0.5 v/fermenter volume/day.

The productivity amounted to 21.7 mg of virus/virus antigen per 1 of fermentation volume.

EXAMPLE 4

Vero cells (ATCC CCL 81) were cultured in a 150-1-fermenter on microcarriers (Cytodex 3 of Pharmacia) at 37° C. up to $2\times10^6$ cells/ml and continuously perfused with medium (DMEM) (0.33 vol/fermenter volume/day) after infection with TBE virus (0.1 pfu/cell).

TABLE 6

| Days post infection | Virus/Virus antigen µg/ml |
|---|---|
| 2 | 0.20 |
| 3 | 1.90 |
| 4 | 2.40 |
| 5 | 4.80 |
| 6 | 5.40 |
| 7 | 4.10 |
| 8 | 4.40 |
| 9 | 3.20 |
| 10 | 4.50 |

The productivity amounted to 14.7 mg of virus/virus antigen per 1 of fermentation volume.

We claim:

1. A continuous perfusion system for the large scale production of virus or virus antigen, said system comprising a perfusion reactor containing virus-infected VERO ATCC CCL 81 cells bound to a microcarrier and maintained under sterile conditions in a perfusion reactor, said cells infected with a virus selected from the group consisting of Flaviviridae and Arenaviridae, wherein from the time the microcarrier loaded with virus-infected cells is introduced into said perfusion reactor onward, serum free media is continuously perfused through said reactor at a temperature of between 34° and 37° C. at a rate of from 0.3 to 10 v/v/day, wherein while said virus-infected cells are adherently bound to said microcarrier in a non-lytic serum free system said cells are metabolically active and viable, and wherein said system continuously produces high concentrations of said virus or virus antigen into said medium for at least 10 days.

2. The perfusion system according to claim 1, wherein said cells are infected with tick borne encephalitis (TBE) virus.

3. The perfusion system according to claim 1, wherein between $1\times10^5$ and $4\times10^5$ of said cells are bound to a cm² of said matrix.

4. A perfusion system according to claim 1, wherein the density of said virus-infected cells in said perfusion reactor is from $2\times10^9$ to $2\times10^{10}$ cells per liter of fermentation volume, and said perfusion reactor is a continuous flow fermenter.

5. A perfusion system according to claim 1, wherein said virus-infected cells bound to said microcarrier are maintained so as to continuously produce a virus or virus antigen in an amount of from 1 µg/ml to 10 µg/ml in said medium.

6. A method for the large scale production of tick-borne encephalitis (TBE) virus and virus antigen comprising the steps of:

(1) infecting Vero ATCC CCL 81 cells, which are bound to a matrix, with TBE virus;

(2) maintaining said virus-infected cells under sterile conditions in a perfusion reactor in which serum-free medium is continuously perfused through said reactor, so as to maintain the viability of said cells and the continuous production of high concentrations of virus or virus antigen into said medium for at least 10 days;

(3) separating said virus and virus antigen-containing medium from said bound cells and concentrating said virus and virus antigen in said medium;

(4) purifying said concentrated virus and virus antigens so as to produce a galenically acceptable preparation containing said purified virus and virus antigens.

7. The method according to claim 6, wherein in step (2), the density of said virus-infected cells in said perfusion reactor is from $2\times10^9$ to $2\times10^{10}$ cells per liter of fermentation volume, and said perfusion reactor is a continuous flow fermenter.

8. The method according to claim 6, wherein in step (2), said cells are maintained so as to continuously produce a virus and virus antigen concentration of from 1 to 10 µg/ml in said medium.

9. A perfusion system for the large scale production of virus or virus antigen, said system comprising a perfusion reactor containing VERO ATCC CCL 81 cells bound to a microcarrier and maintained under sterile conditions in a perfusion reactor, said cells infected with Tick Borne Encephalitis (TBE) virus, wherein from the time the microcarrier loaded with virus-infected cells is introduced into said perfusion reactor onward, serum free media is continuously perfused through said reactor, wherein while said virus-infected cells are bound to said microcarrier in a non-lyric serum free system said cells are metabolically active and viable, and wherein said system continuously produces high concentrations of said virus or virus antigen into said medium for at least 10 days.

* * * * *